US005824195A

United States Patent [19]

Kimae et al.

[11] Patent Number: 5,824,195

[45] Date of Patent: Oct. 20, 1998

[54] PROCESS FOR DISTILLING CRUDE ACRYLIC SILANE SOLUTION

[75] Inventors: Yoichi Kimae; Katsuyoshi Tsuchiya; Takashi Matsuo; Kiyoto Fukuda, all of Kumamoto, Japan

[73] Assignee: Chisso Corporation, Osaka-fu, Japan

[21] Appl. No.: 670,442

[22] Filed: Jun. 26, 1996

[30] Foreign Application Priority Data

| | | | |
|---|---|---|---|
| Jul. 10, 1995 | [JP] | Japan | 7-196966 |
| Aug. 1, 1995 | [JP] | Japan | 7-216792 |
| Aug. 28, 1995 | [JP] | Japan | 7-242535 |
| Aug. 30, 1995 | [JP] | Japan | 7-245484 |
| Sep. 7, 1995 | [JP] | Japan | 7-257020 |
| Apr. 18, 1996 | [JP] | Japan | 8-121047 |

[51] Int. Cl.[6] .................. B01D 3/34; C07F 7/20

[52] U.S. Cl. .................. 203/8; 203/59; 203/65; 556/401

[58] Field of Search .................. 203/8, 91, 59, 203/65; 556/401, 438, 442

[56] References Cited

U.S. PATENT DOCUMENTS

| | | | |
|---|---|---|---|
| 3,258,477 | 6/1966 | Plueddemann et al. | 106/97 |
| 3,816,267 | 6/1974 | Chuang | 203/8 |
| 4,709,067 | 11/1987 | Chu et al. | 560/440 |
| 5,103,032 | 4/1992 | Turner et al. | 203/8 |

FOREIGN PATENT DOCUMENTS

| | | |
|---|---|---|
| 52-34606 | 9/1977 | Japan . |
| 57-300 | 1/1982 | Japan . |
| 57-61015 | 12/1982 | Japan . |
| 7-109283 | 4/1995 | Japan . |

*Primary Examiner*—Virginia Manoharan
*Attorney, Agent, or Firm*—Wenderoth, Lind & Ponack, L.L.P.

[57] ABSTRACT

A process for distilling a crude acrylic silane solution particularly containing impurities in a commercial scale for separating acrylic silane in the presence of a hindered phenol and/or amine as polymerization inhibitor, the process being improved by using simultaneously a dialkyldithiocarbamic acid copper and/or N-nitrosophenylhydroxylamine salt as synergistic polymerization inhibitor.

13 Claims, 1 Drawing Sheet

4
6
3
8
2
5
1
7

PROCESS FOR DISTILLING CRUDE ACRYLIC SILANE SOLUTION

BACKGROUND OF THE INVENTION

1. Field of the Invention

The present invention relates to a process for distilling a crude chlorosilane or acetoxysilane having a methacyloxy group or acryloxy group (in the present specification, the chlorosilane or acetoxysilane is referred to as acrylic silane). More specifically, the present invention relates to a process for distilling a crude acrylic silane containing impurities in which process the spontaneous polymerization of the acrylic silane caused at a distillation in a commercial scale can efficiently be repressed.

2. Description of the Related Art

Acrylic silanes are effective for many uses such as silane coupling agents, starting materials for silane coupling agents, starting materials for polysiloxanes, terminating agents in the production of polysiloxanes, surface treating agents for several substrates, and modifiers for several resins.

Acrylic silanes having such a high utility are generally obtained by subjecting an acrylic acid ester or methacrylic acid ester to a hydrosilylation reaction with a hydrosilane compound in the presence of a transition metal catalyst such as platinum and then subjecting the resulting reaction solution to a distillation under a reduced pressure for purification.

As an example of such process for producing an acrylic silane, a method is described in Japanese Patent Publication No. Hei 6-51707 in which an aryl methacrylate is reacted with methyldichlorosilane in the presence of platinum catalyst and then the reaction product is distilled under a reduced pressure to obtain 3-methacryloxypropyldimethylchlorosilane.

However, acrylic silanes have a defect of being apt to be spontaneously polymerized by heat in the steps of their synthetic reaction, distillation, storage, and transportation, whereas the acrylic silanes can be used as starting materials for producing several functional materials due to their high polymerizability.

Accordingly, how to prevent the spontaneous polymerization of acrylic silanes becomes a most important subject when acrylic silanes are unavoidably heated above room temperature in the step of their synthetic reaction or distillation after the synthetic reaction. In order to prevent the spontaneous polymerization of acrylic silanes, a polymerization inhibitor is usually added to a starting material or reaction solution of an acrylic silane (in the present specification, the starting material or reaction solution of an acrylic silane are sometimes inclusively referred to as acrylic silane solution). For example, a phenol type polymerization inhibitor such as hydroquinone or methoquinone has preferably been used.

However, phenol type polymerization inhibitors have a defect of causing a condensation reaction with the acrylic silane in which a chlorine atom is linked to a silicon atom (hereinafter referred to as chlorosilane) to lose their ability of inhibiting polymerization. This fact is also described in Japanese Patent Publication No. Hei 6-51707 and a paper by Efimov et al. (Zh. Obsch. Khim. (1991) 61 (10) 2244–53).

When a polymerization inhibitor to be used is selected, the efficiency of the polymerization inhibitor is usually judged by using a methacrylic acid ester or acrylic acid ester and examining the extent in which the spontaneous polymerization of the ester is repressed with the added polymerization inhibitor when the ester is heated to a temperature at which the spontaneous polymerization is caused in the absence of the inhibitor.

While such examination is usually performed by a table test in beaker scale, it is known from the results of the examination that hindered phenols represented by 2,6-di-t-butyl-4-methylphenol and amines represented by N,N'-diphenyl-p-phenylenediamine or phenothiazine are extremely efficient as polymerization inhibitor for acrylic silane.

However, the hindered phenols and amines have a defect that they become impossible to sufficiently repress the spontaneous polymerization of acrylic silane when the distillation is expanded to a commercial scale, whereas they are effective at a table test.

As a result of diligent investigation by the present inventors on that problem, it has been found that there are two kinds of polymerization, homogeneous polymerization and proliferous polymerization, in the form of spontaneous polymerization of acrylic silane. In the homogeneous polymerization, the viscosity of acrylic silane solution is gradually increased with the progress of polymerization of acrylic silane and the solution is finally solidified in a pudding state. In contrast, in the proliferous polymerization, insoluble polymers resembling popcorn in shape are formed in the acrylic silane solution by an abnormal reaction in free radical polymerization, and the polymers are steadily grown and expanded. When an acrylic silane caused proliferous polymerization, the volume of the polymer from the acrylic silane becomes more than twice as large as that of monomer. Thus, it not only causes blocking of the reaction apparatus and piping, but also leads to a serious accident such as destruction of the distillation apparatus.

Although the reason is not clear, the polymerization is very strongly inclined toward the homogeneous polymerization and the proliferous polymerization can hardly be noticed in the table test mentioned above. Accordingly, even when the performance of polymerization inhibitors were examined by the table test as mentioned above, only their effect on the homogeneous polymerization can be found. Thus if a scale-up of the distillation was made based on the results of the table test, the proliferous polymerization can not be repressed. Accordingly, when the scale-up is made to a commercial scale, it is necessary to find a polymerization inhibitor which can prevent both homogeneous polymerization and proliferous polymerization, and to establish a process for producing acrylic silane using the inhibitor.

Further, since apparatuses generally used for distilling a crude acrylic silane solution are composed of a distillation still in which a crude acrylic silane solution obtained in the step of synthetic reaction is heated under a reduced pressure to evaporate and a distillation column in which the evaporated crude acrylic silane is purified, when a polymerization inhibitor was added in the distillation still, the inhibitor is effective for repressing the spontaneous polymerization of acrylic silane in the distillation still. However, the inhibitor does not have the effect of repressing the spontaneous polymerization of vapor or drops of acrylic silane (hereinafter inclusively referred to as acrylic silane vapor) passing through inside the distillation column. This is because the polymerization inhibitor added in the acrylic silane solution is not evaporated in the distillation still and thus the inhibitor does not exist inside the distillation column.

As a method for repressing the spontaneous polymerization inside the distillation column, there is a method in which a polymerization inhibitor having a boiling point similar to or slightly lower than that of acrylic silane is used. However, this method has a defect that a large amount of the polymerization inhibitor is mixed in the product after distillation to deteriorate the quality of the product, and the type of polymerization inhibitor must be properly selected depending on the boiling point of acrylic silane.

There is a method in which oxygen or laughing gas is used. However, it is the present situation that the use of only oxygen or laughing gas can not sufficiently prevent the spontaneous polymerization.

SUMMARY OF THE INVENTION

An object of the present invention is to solve the defects in the prior art mentioned above and to provide a process for distilling a crude acrylic silane solution which can efficiently repress the spontaneous polymerization of acrylic silane at the time of distillation for its purification.

The present invention comprises the following aspects (1) to (12):

(1) In the process for distilling a crude acrylic silane solution for separating acrylic silane expressed by formula (I) by distilling the crude acrylic silane solution in the presence of a hindered phenol and/or amine as polymerization inhibitor, the improvement wherein the process comprises adding simultaneously a dialkyldithiocarbamic acid copper and/or N-nitrosophenylhydroxylamine salt as further polymerization inhibitor to the solution $$CH_2{=}CR^1COO(X)_mSiR^2_nR^3_{3-n} \quad (I)$$

wherein $R^1$ represents hydrogen atom, an alkyl group having 1 to 8 carbon atoms, or an aryl group having 6 to 10 carbon atoms, X represents $CH_2CH_2O$ or $CH_2$, or combination of these two groups, m is an integer of 1 to 12, $R^2$ represents a hydrolyzable group, $R^3$ represents an alkyl group, alkenyl group, or aryl group having 1 to 12 carbon atoms, and n is an integer of 1 to 3.

(2) The process for distilling a crude acrylic silane solution recited in (1) above wherein the N-nitrosophenylhydroxylamine salt is a compound expressed by formula (II)

$$(R^4N(NO)O)_pY_q \quad (II)$$

wherein $R^4$ represents an aryl group having 6 to 10 carbon atoms, p is an integer of 1 to 4, q is an integer of 1 to 4, and Y represents a cation atom or molecule.

(3) The process for distilling a crude acrylic silane solution recited in (1) above wherein the dialkyldithiocarbamic acid copper is a compound expressed by formula (III)

$$(R^5_2NC({=}S)S)_2Cu \quad (III)$$

wherein $R^5$ represents an alkyl group having 1 to 5 carbon atoms.

(4) The process for distilling a crude acrylic silane solution recited in (1) above wherein the hindered phenol is a compound having, in the vicinity of a hydroxyl group of an aromatic ring, at least one substituent causing steric hindrance in the compound.

(5) The process for distilling a crude acrylic silane solution recited in (1) above wherein the N-nitrosophenylhydroxylamine salt is added in the vapor generated at the time of distillation.

(6) In the process for distilling a crude acrylic silane solution for separating acrylic silane expressed by formula (I) by distilling the crude acrylic silane solution in the presence of a hindered phenol and/or amine as polymerization inhibitor by using a distillation apparatus provided with a distillation still and a distillation column arranged above the distillation still, the improvement wherein the process comprises conducting the distillation while adding a liquid mixture containing a N-nitrosophenylhydroxylamine salt as further polymerization inhibitor from an upper portion of the distillation column $$CH_2{=}CR^1COO(X)_mSiR^2_nR^3_{3-n} \quad (I)$$

wherein $R^1$ represents hydrogen atom, an alkyl group having 1 to 8 carbon atoms, or an aryl group having 6 to 10 carbon atoms, X represents $CH_2CH_2O$ or $CH_2$, or combination of these two groups, m is an integer of 1 to 12, $R^2$ represents a hydrolyzable group, $R^3$ represents an alkyl group, alkenyl group, or aryl group having 1 to 12 carbon atoms, and n is an integer of 1 to 3.

(7) The process for distilling a crude acrylic silane solution recited in (6) above wherein the liquid mixture contains a hindered phenol and/or amine, and a N-nitrosophenylhydroxylamine salt.

(8) The process for distilling a crude acrylic silane solution recited in (6) above wherein the N-nitrosophenylhydroxylamine salt is a compound expressed by formula (II)

$$(R^4N(NO)O)_pY_q \quad (II)$$

wherein $R^4$ represents an aryl group having 6 to 10 carbon atoms, p is an integer of 1 to 4, q is an integer of 1 to 4, and Y represents a cation atom or molecule.

(9) The process for distilling a crude acrylic silane solution recited in (6) above wherein the hindered phenol is a compound having, in the vicinity of a hydroxyl group of an aromatic ring, at least one substituent giving steric hindrance in the compound.

(10) The process for distilling a crude acrylic silane solution recited in (6) above wherein the distillation is conducted while having present, in the distillation still, a dialkyldithiocarbamic acid copper and/or N-nitrosophenylhydroxylamine salt.

(11) The process for distilling a crude acrylic silane solution recited in (10) above wherein the dialkyldithiocarbamic acid copper is a compound expressed by formula (III)

$$(R^5_2NC({=}S)S)_2Cu \quad (III)$$

wherein $R^5$ represents an alkyl group having 1 to 5 carbon atoms.

(12) The process for distilling a crude acrylic silane solution recited in (10) wherein the hindered phenol is a compound having, in the vicinity of a hydroxyl group of an aromatic ring, at least one substituent giving steric hindrance in the compound.

DESCRIPTION OF THE PREFERRED EMBODIMENTS

Figure 1:
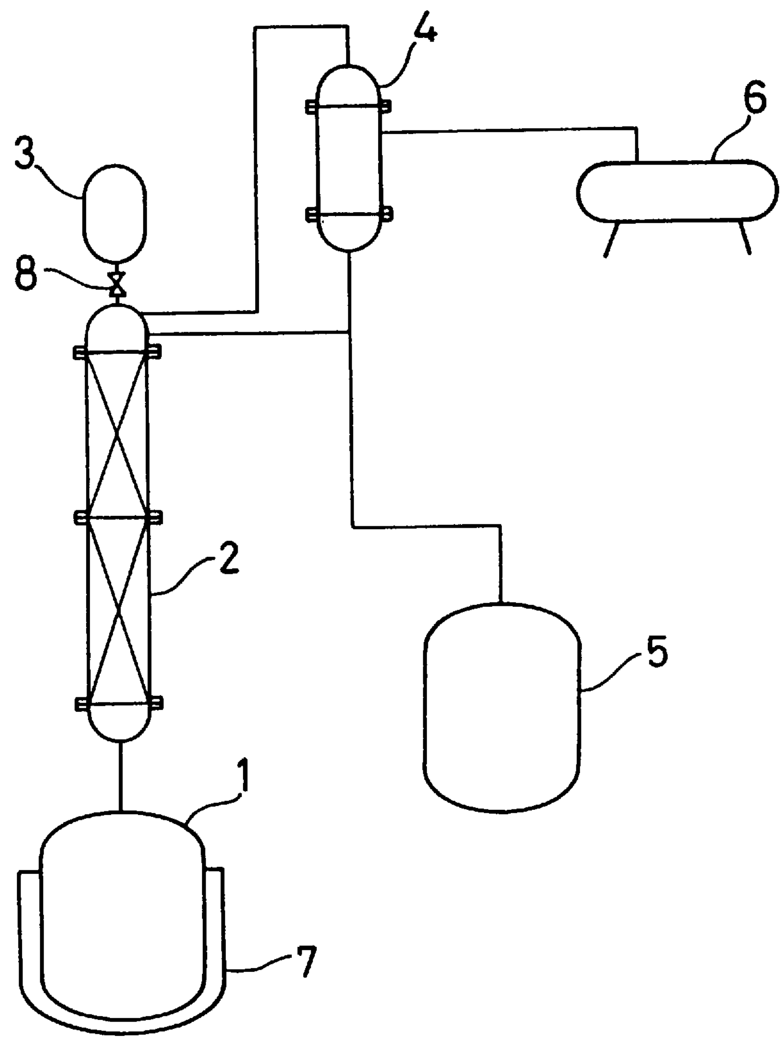
FIG. 1 is a schematic diagram of an apparatus suitable for carrying out the process for distilling a crude acrylic silane solution containing impurities for separating acrylic silane according to the present invention.

The present invention is particularly concerned with a process for distilling a crude acrylic silane solution containing impurities in a commercial scale for purification wherein a hindered phenol and/or amine is used for preventing homogeneous polymerization of acrylic silane and further a dialkyldithiocarbamic acid copper and/or N-nitrosophenylhydroxyl amine salt is simultaneously used for preventing proliferous polymerization of acrylic silane.

The distillation process of the present invention is efficient for repressing the spontaneous polymerization of acrylic silanes expressed by formula (I)

$$CH_2{=}CR^1COO(X)_mSiR^2_nR^3_{3-n} \quad (I)$$

wherein $R^1$ represents hydrogen atom, an alkyl group having 1 to 8 carbon atoms, or an aryl group having 6 to 10 carbon atoms, X represents $CH_2CH_2O$ or $CH_2$, or combination of these two groups, m is an integer of 1 to 12, $R^2$ represents a hydrolyzable group, $R^3$ represents an alkyl group, alkenyl group, or aryl group having 1 to 12 carbon atoms, and n is an integer of 1 to 3.

Among the acrylic silanes, the present invention is particularly effective for the compounds having the structure expressed by the formula (I) wherein $R^2$ is —OC(=O)$R^5$ (in which $R^5$ represents an alkyl group having 1 to 8 carbon atoms, alkenyl group having 1 to 8 carbon atoms, alkynyl group having 1 to 8 carbon atoms, or aryl group having 6 to 10 carbon atoms); preferably —OC(=O)$CR^6{=}CH_2$ (in which $R^6$ represents an alkyl group having 1 or 2 carbon atoms or hydrogen atom) or halogen atom; and more desirably —OC(=O)$CH_3$ or chlorine atom.

Specifically, the examples of such acrylic silane include 3-methacryloxypropyltrichlorosilane, 3-methacryloxypropylmethyldichlorosilane, 3-methacryloxypropyldimethylchlorosilane, 3-acryloxypropyltrichlorosilane, 3-acryloxypropylmethyldichlorosilane, 3-acryloxypropyldimethylchlorosilane, 3-methacryloxypropyldimethylacetoxysilane, 3-methacryloxypropyldimethylmethacryloxysilane, 3-acryloxypropyldimethylacetoxysilane, and 3-acryloxypropyldimethylacryloxysilane.

Distillation for purification of acrylic silane in the present invention is conducted in the presence of a hindered phenol and/or amine.

As the hindered phenol used in the present invention, 2,6-di-t-butyl-4-methylphenol and 2,6-di-t-butyl-4-dimethylaminomethylphenol can specifically be mentioned as examples.

As the amine used in the present invention, N,N'-diphenyl-p-phenylenediamine and phenothiazine can specifically be mentioned as examples.

Amount of the hindered phenol and/or amine used in the present invention is preferably 1 to 100,000 ppm (converted into weight) and more desirably 10 to 5,000 ppm (converted into weight) based on acrylic silane.

In the present invention, the hindered phenol and amine may be used alone or in combination of at least one of the hindered phenols with at least one of the amines.

As specific methods for using such a phenol or amine compound, there can be mentioned as examples a method in which the compound is added to a starting material for an acrylic silane immediately prior to the step of synthetic reaction of the acrylic silane; a method in which the compound is mixed with a starting material for an acrylic silane in advance; a method in which the compound is added to a reaction mixture of an acrylic silane immediately prior to the step of distillation for its purification; a method in which the compound is supplied from an upper portion of the distillation column.

Whereas the hindered phenols and amines have an excellent effect on repressing homogeneous polymerization, they are not effective for repressing proliferous polymerization. Accordingly, when proliferous polymerization is caused, a dialkyldithiocarbamic acid copper and/or N-nitrosophenylhydroxylamine salt must be used together.

Whereas the dialkyldithiocarbamic acid copper and/or N-nitrosophenylhydroxylamine salt used in the present invention is not so effective for repressing spontaneous polymerization of acrylic silane in a table test, it exhibits a remarkably excellent ability of repressing the spontaneous polymerization when used in the present invention.

Such N-nitrosophenylhydroxylamine salt is expressed by formula (II)

$$(R^4N(NO)O)_pY_q \quad (II)$$

wherein $R^4$ represents an aryl group having 6 to 10 carbon atoms, p is an integer of 1 to 4, q is an integer of 1 to 4, and Y represents a cation atom or molecule.

As the amine salt,-N-nitrosophenylhydroxylamine ammonium salt, N-nitrosophenylhydroxylamine sodium salt, N-nitrosophenylhydroxylamine potassium salt, and N-nitrosophenylhydroxylamine aluminum salt can specifically be mentioned as examples.

Dialkyldithiocarbamic acid copper is expressed by formula (III)

$$(R^5_2NC({=}S)S)_2Cu \quad (III)$$

wherein $R^5$ represents an alkyl group having 1 to 5 carbon atoms.

As the acid copper, dimethyldithiocarbamic acid copper, diethyldithiocarbamic acid copper, di-n-propyldithiocarbamic acid copper, diisopropyldithiocarbamic acid copper, and di-n-butyldithiocarbamic acid copper can specifically be mentioned as examples.

These amine salt and/or acid copper may be used alone or in combination thereof.

As specific methods for using such an amine salt and acid copper, there can be mentioned as examples a method in which such a compound is added to a starting material for an acrylic silane immediately prior to the step of synthetic reaction of the acrylic silane; a method in which such a compound is mixed with a starting material for an acrylic silane in advance; a method in which such a compound is added to a reaction mixture of an acrylic silane immediately prior to the step of distillation for its purification; and a method in which such a compound is supplied from an upper portion of the distillation column.

Amount of the dialkyldithiocarbamic acid copper and/or N-nitrosophenylhydroxylamine salt used in the present invention is preferably 1 to 100,000 ppm (converted into weight) and more desirably 10 to 5,000 ppm (converted into weight) based on acrylic silane.

Whereas the dialkyldithiocarbamic acid copper and N-nitrosophenylhydroxylamine salt have an excellent effect on repressing proliferous polymerization, they are not effective for repressing homogeneous polymerization. Accordingly, the acid copper and amine salt must be used together with the hindered phenol and/or amine.

When a crude acrylic silane solution is subjected to a distillation for purification in a commercial scale, a distillation apparatus comprising a distillation still and a distillation column is generally used to increase the purity of acrylic silane. When such apparatus is used, the distillation is preferably conducted while supplying a liquid mixture containing a N-nitrosophenylhydroxylamine salt from an upper portion of the distillation column.

This is because the spontaneous polymerization of acrylic silane vapor inside the distillation column can efficiently be repressed by continuously supplying from an upper portion of the distillation column a liquid mixture in which a N-nitrosophenylhydroxylamine salt is dispersed or solved.

Method for supplying the liquid mixture is not specifically restricted, and a dropping method or spray method may be used.

Since N-nitrosophenylhydroxylamine salts are very hardly mixed as contaminant in acrylic silane purified by distillation, the amine salts do not deteriorate the quality of the product.

N-nitrosophenylhydroxylamine salt used for the liquid mixture is also expressed by the same formula (II) as mentioned above $$(R^4N(NO)O)_pY_q \quad \text{(II)}$$

(in which $R^4$, p, q, and Y are the same as mentioned above.)

As the amine salt to be included in the liquid mixture, N-nitrosophenylhydroxylamine ammonium salt, N-nitrosophenylhydroxylamine sodium salt, N-nitrosophenylhydroxylamine potassium salt, and N-nitrosophenylhydroxylamine aluminum salt can also be specifically mentioned as examples. These amine salts may be used alone or in combination thereof.

Amount of the N-nitrosophenylhydroxylamine salt to be fed as a component of the liquid mixture is suitably 0.1 to 10,000 ppm (converted into weight) and more desirably 1 to 100 ppm (converted into weight) based on the amount of acrylic silane evaporated per hour.

When a crude acrylic silane solution is distilled for purification in a commercial scale, there is a danger that the ratio of proliferous polymerization is higher than that of homogeneous polymerization, in the spontaneous polymerization of acrylic silane caused in distillation column. Accordingly, a liquid mixture containing a N-nitrosophenylhydroxylamine salt which can prevent the proliferous polymerization is preferably supplied to a distillation column from its upper portion. However, it is especially desirable to supply, from an upper portion of a distillation column, a liquid mixture containing a N-nitrosophenylhydroxylamine salt as well as a hindered phenol and/or amine to prevent the homogeneous polymerization at the same time.

As the hindered phenol and amine, 2,6-di-t-butyl-4-methylphenol, 2,6-di-t-butyl-4-dimethylaminomethylphenol, N,N'-diphenyl-p-phenylenediamine, and phenothiazine can specifically be mentioned as examples. These compounds may be used alone or in combination thereof.

Hindered phenol and amine can be suppressed from being mixed in the acrylic silane purified by distillation, by selecting a compound having a suitable boiling point.

While the amount of the hindered phenol and/or amine to be supplied as a component included in the liquid mixture depends on the shape of distillation column, it is preferably 0.1 to 10,000 ppm (converted into weight) and more desirably 1 to 100 ppm (converted into weight) based on the acrylic silane evaporated per hour.

While the liquid in which the N-nitrosophenylhydroxylamine salt as well as the hindered phenol and/or amine are dissolved to form the liquid mixture is not specifically restricted, the liquid is preferably one which does not react with acrylic silane or polymerization inhibitor and is not mixed in the acrylic silane purified by distillation. The liquid having a boiling point higher than that of acrylic silane to be distilled for purification or pure acrylic silane is especially preferable. Specifically, 3-methacryloxypropyldimethylchlorosilane and a mineral oil can be mentioned as examples of the liquid.

Even when a distillation apparatus comprising a distillation still and distillation column is used, a hindered phenol and/or amine must be included in the crude acrylic silane solution in the distillation still, and the hindered phenol and/or amine is included preferably together with a dialkyldithiocarbamic acid copper and/or N-nitrosophenylhydroxylamine salt in the crude acrylic silane.

In the distillation process of the present invention, a gas in which molecular oxygen is diluted with an inert gas, or air may be introduced within the apparatus.

Now, an embodiment of the distillation apparatus which can be used in the present invention will be described with reference to the drawing. While the distillation process of the present invention is most preferably performed by using such a distillation apparatus as shown in the drawing, it does not need to be restricted to use of such apparatus unless it departs from the spirit of the present invention.

Crude acrylic silane solution obtained by a synthetic reaction (and which contains a hindered phenol and/or amine; or a hindered phenol and/or amine as well as a dialkyldithiocarbamic acid copper and/or N-nitrosophenylhydroxylamine salt) is placed in distillation still (1) and then heated under a reduced pressure to evaporate acrylic silane. Pressure reduction is achieved by pressure reducing pump (6), and heating is performed by circulating a heat transfer medium through jacket (7) arranged around distillation still (1). Evaporated acrylic silane is led to distillation column (2), flowed upward in distillation column (2), discharged from an upper portion of distillation column (2), and then introduced in condenser (4).

On the other hand, a liquid mixture containing a N-nitrosophenylhydroxylamine salt (or a N-nitrosophenylhydroxylamine salt, and a hindered phenol and/or amine) is placed in tank (3) for a liquid mixture to be fed from the top of the column, and the liquid mixture is supplied in distillation column (2) while controlling its flow rate with flow rate control valve (8).

After liquefied with condenser (4), acrylic silane is stored in tank (5) for distillate. According to circumstances, the acrylic silane stored in the tank (5) is introduced to an upper portion of distillation column (2) and again subjected to distillation for purification.

Now, the present invention will be described in more detail with reference to Examples, Comparative Examples, and Referential Examples. However, it should be understood that the present invention is by no means restricted by such specific Examples.

EXAMPLE 1

Acrylic silane solution containing, as its main component, 3-methacryloxypropyldimethylchlorosilane was produced by a known method from aryl methacrylate and dimethylchlorosilane in the presence of platinum catalyst. In 6.54 kg of the acrylic silane solution were dissolved 0.66 g of phenothiazine and 0.66 g of dimethyldithiocarbamic acid copper, and the solution thus obtained was subjected to a distillation for purification with a simple distillation apparatus provided with no distillation column. After low boiling point components mainly composed of aryl methacrylate were distilled off at a pressure of 40 kPa and at a temperature at the top of the column of 30° to 50° C., the fraction of 3-methacryloxypropyldimethylchlorosilane was obtained at a pressure of 15 kPa and at a temperature at the top of the column of 65° to 75° C. During the distillation, the polymerization which increased the viscosity of the contents of the distillation still was not observed and the formation of the products of proliferous polymerization was not noticed, either.

EXAMPLE 2

Distillation procedures for purification in Example 1 were repeated except that 0.66 g of 2,6-di-t-butyl-4-methylphenol was added to the acrylic silane solution obtained by the same way as described in Example 1. During the distillation procedures, the polymerization which increased the viscosity of the contents of the distillation still was not observed and the formation of the products of proliferous polymerization was not noticed, either.

EXAMPLE 3

Distillation procedures for purification in Example 1 were repeated except that 0.66 g of 2,6-di-t-butyl-4-dimethylphenol was used in place of phenothiazine. During the distillation procedures, the polymerization which increased the viscosity of the contents of the distillation still was not observed and the formation of the products of proliferous polymerization was not noticed, either.

EXAMPLE 4

Acrylic silane solution containing, as its main component, 3-methacryloxypropyldimethylchlorosilane was produced by a known method from aryl methacrylate and dimethylchlorosilane in the presence of platinum catalyst. In 6.28 kg of the acrylic silane solution were dissolved 6.5 g of N-nitrosophenylhydroxylamine aluminum salt and 65.7 g of phenothiazine, and the solution thus obtained was subjected to a distillation for purification with a simple distillation apparatus provided with no distillation column. After low boiling point components mainly composed of aryl methacrylate were distilled off at a pressure of 40 kPa and at a temperature at the top of the column of 30° to 50° C., the fraction of 3-methacryloxypropyldimethylchlorosilane was obtained at a pressure of 15 kPa and at a temperature at the top of the column of 85° to 90° C. During the distillation, the polymerization which increased the viscosity of the contents of the distillation still was not observed and the formation of the products of proliferous polymerization was not noticed, either.

EXAMPLE 5

Distillation procedures for purification in Example 4 were repeated except that 0.66 g of 2,6-di-t-butyl-4-methylphenol was added to the acrylic silane solution obtained in the same way as described in Example 4. During the distillation procedures, the polymerization which increased the viscosity of the contents of the distillation still was not observed and the formation of the products of proliferous polymerization was not noticed, either.

EXAMPLE 6

Distillation procedures for purification in Example 4 were repeated except that 0.66 g of 2,6-di-t-butyl-4-dimethylphenol was used in place of phenothiazine. During the distillation procedures, the polymerization which increased the viscosity of the contents of the distillation still was not observed and the formation of the products of proliferous polymerization was not noticed, either.

Comparative Example 1

Distillation procedures for purification in Example 1 were repeated except that 68 g of phenothiazine was used instead of using phenothiazine together with dimethyldithiocarbamic acid copper. After low boiling point components mainly composed of aryl methacrylate were distilled off at a pressure of 40 kPa and at a temperature at the top of the column of 30° to 50° C., the polymers by proliferous polymerization were formed in the distillation still and were steadily grown so that distillation procedures became impossible to continue.

Comparative Example 2

Distillation procedures for purification in Example 1 were repeated except that 0.66 g of phenothiazine and 0.66 g of 2,6-di-t-g-dimethylaminomethylphenol were used instead of using phenothiazine and dimethyldithiocarbamic acid copper. In the course of the time when low boiling point components mainly composed of aryl methacrylate were distilled off at a pressure of 50 kPa and at a temperature at the top of the column of 30° to 40° C., the products of proliferous polymerization were formed in the distillation still and thus distillation procedures were discontinued.

Comparative Example 3

Distillation procedures for purification in Example 1 were repeated except that 0.75 g of phenothiazine and 0.75 g of anhydrous cupric chloride were used in place of phenothiazine and dimethyldithiocarbamic acid copper. After low boiling point components mainly composed of aryl methacrylate were distilled off at a pressure of 40 kPa and at a temperature at the top of the column of 30° to 50° C., the products of proliferous polymerization were formed in the distillation still and were steadily grown so that distillation procedures became impossible to continue.

Referential Example (Beaker Scale Test of Comparative Example 1)

Acrylic silane solution containing, as its main component, 3-methacryloxypropyldimethylchlorosilane was produced by a known method from aryl methacrylate and dimethylchlorosilane in the presence of platinum catalyst. In 506 g of the acrylic silane solution was dissolved 5.1 g of phenothiazine, and the solution thus obtained was subjected to a distillation for purification. After low boiling point components mainly composed of aryl methacrylate were distilled off at a pressure of 40 kPa and at a temperature at the top of the column of 30° to 60° C., the fraction of 3-methacryloxypropyldimethylchlorosilane was obtained at a pressure of 15 kPa and at a temperature at the top of the column of 65° to 75° C. During the distillation, the polymerization which increased the viscosity of the contents of the distillation still was not observed and the formation of the products of proliferous polymerization was not noticed, either.

EXAMPLE 7

Acrylic silane solution containing, as its main component, 3-methacryloxypropyldimethylchlorosilane was produced by a known method from aryl methacrylate and dimethylchlorosilane in the presence of platinum catalyst, and subjected to a distillation for purification with such a distillation apparatus as shown in the drawing.

First, about 5 kg of the acrylic silane solution and 0.5 g of 2,6-di-t-butyl-4-dimethylaminophenol were charged in distillation still (1). After low boiling point components mainly composed of aryl methacrylate were distilled off by reducing the pressure inside the apparatus to 30 kPa and controlling the conditions of distillation column (2) so that the temperature at the top of the column was 60° to 85° C., the pressure was further reduced to 15 kPa and the conditions of the column were controlled again so that the temperature at the top of the column was 69° to 75° C. to obtain the fraction of 3-methacryloxypropyldimethylchlorosilane.

During the distillation, a solution in which N-nitrosophenylhydroxylamine aluminum salt was dissolved in 3-methacryloxypropyldimethylchlorosilane so that the content of the aluminum salt was 2% by weight ratio was supplied from the top portion of distillation column (2) having an inside diameter of about 50 cm and filled up with a "Heli-Pack".

After finishing the distillation, inside of distillation column (2) was inspected to find no products of spontaneous polymerization of acrylic silane.

EXAMPLE 8

Distillation was conducted according to the method in Example 7 except in that a solution in which N-nitrosophenylhydroxylamine aluminum salt was dissolved in mineral oil (NeoSK-OIL330 produced by Soken Chemical & Engineering Co., Ltd.) so that the content of the aluminum salt was 2% by weight ratio was added from the top portion of distillation column (2) instead of a solution in which N-nitrosophenylhydroxylamine aluminum salt was dissolved in 3-methacryloxypropyldimethylchlorosilane so that the content of the aluminum salt was 2% by weight ratio as in Example 7.

After finishing the distillation, inside of distillation column (2) was inspected to find no products of spontaneous polymerization of acrylic silane.

EXAMPLE 9

Acrylic silane solution containing, as its main component, 3-methacryloxypropyldimethylchlorosilane was produced by a known method from aryl methacrylate and dimethylchlorosilane in the presence of platinum catalyst, and subjected to a distillation for purification with such a distillation apparatus as shown in the drawing.

First, 6.28 kg of the acrylic silane solution, 65.7 g of phenothiazine, and 6.5 g of N-nitrosophenylhydroxylamine aluminum salt were charged in distillation still (1). After low boiling point components mainly composed of aryl methacrylate were distilled off by reducing the pressure inside the apparatus to 30 kPa and controlling the conditions of distillation column (2) so that the temperature at the top of the column was 60° to 85° C., the pressure was further reduced to 15 kPa and the conditions of the column were controlled again so that the temperature at the top of the column was 69° to 75° C. to obtain the fraction of 3-methacryloxypropyldimethylchlorosilane.

During the distillation, a solution in which N-nitrosophenyl hydroxylamine aluminum salt was dissolved in 3-methacryloxypropyldimethylchlorosilane so that the content of the aluminum salt was 2% by weight ratio was supplied from the top portion of distillation column (2) having an inside diameter of about 50 cm and filled up with a "Heli-Pack".

When the distillation was being conducted, the polymerization which increased the viscosity of the acrylic silane solution in distillation still (1) was not observed and the formation of the products of proliferous polymerization was not noticed, either. After finishing the distillation, the inside of distillation column (2) was inspected to find no products of homogeneous polymerization or proliferous polymerization of acrylic silane.

EXAMPLE 10

Distillation was conducted according to the method in Example 9 except in that a solution in which N-nitrosophenylhydroxylamine aluminum salt was dissolved in mineral oil (NeoSK-OIL330 produced by Soken Chemical & Engineering Co., Ltd.) so that the content of the aluminum salt was 2% by weight ratio was added from the top portion of distillation column (2) instead of a solution in which N-nitrosophenylhydroxylamine aluminum salt was dissolved in 3-methacryloxypropyldimethylchlorosilane so that the content of the aluminum salt was 2% by weight ratio as in the case of Example 9.

When the distillation was being conducted, the polymerization which increased the viscosity of the acrylic silane solution in distillation still (1) was not observed and the formation of the products of proliferous polymerization was not noticed, either. After finishing the distillation, inside of distillation column (2) was inspected to find no products of homogeneous polymerization or proliferous polymerization of acrylic silane.

EXAMPLE 11

Acrylic silane solution containing, as its main component, 3-methacryloxypropyldimethylchlorosilane was synthesized by a known method from aryl methacrylate and dimethylchlorosilane in the presence of platinum catalyst, and subjected to a distillation for purification with such a distillation apparatus as shown in the drawing.

First, 5 kg of the acrylic silane solution, 0.5 g of phenothiazine, and 0.5 g of dimethyldithiocarbamic acid copper were charged in distillation still (1). After low boiling point components mainly composed of aryl methacrylate were distilled off by reducing the pressure inside the apparatus to 30 kPa and controlling the conditions of distillation column (2) so that the temperature at the top of the column was 60° to 85° C., the pressure was further reduced to 15 kPa and the conditions of the column were controlled again so that the temperature at the top of the column was 69° to 75° C. to obtain the fraction of 3-methacryloxypropyldimethylchlorosilane.

During the distillation, a solution in which N-nitrosophenyhydroxylamine aluminum salt was dissolved in 3-methacryloxypropyldimethylchlorosilane so that the content of the aluminum salt was 2% by weight ratio was supplied from the top portion of distillation column (2) having an inside diameter of about 50 cm and filled up with a "Heli-pack".

When the distillation was being conducted, the polymerization which increased the viscosity of the acrylic silane solution in distillation still (1) was not observed and the formation of the products of proliferous polymerization was not noticed, either. After finishing the distillation, the inside of distillation column (2) was inspected to find no products of homogeneous polymerization or proliferous polymerization of acrylic silane.

EXAMPLE 12

Distillation was conducted according to the method in Example 11 except in that a solution in which N-nitrosophenylhydroxylamine aluminum salt was dissolved in mineral oil (NeoSK-OIL330 produced by Soken Chemical & Engineering Co., Ltd.) so that the content of the aluminum salt was 2% by weight ratio was added from the top portion of distillation column (2) instead of a solution in which N-nitrosophenylhydroxylamine aluminum salt was dissolved in 3-methacryloxypropyldimethylchlor osilane so that the content of the aluminum salt was 2% by weight ratio in Example 11.

When the distillation was being conducted, the polymerization which increased the viscosity of the acrylic silane solution in distillation still (1) was not observed and the formation of the products of proliferous polymerization was not noticed, either. After finishing the distillation, inside of distillation column (2) was inspected to find no products of homogeneous polymerization or proliferous polymerization of acrylic silane.

EXAMPLE 13

Acrylic silane solution containing, as its main component, 3-methacryloxypropyldimethylchlorosilane was produced by a known method from aryl methacrylate and dimethylchlorosilane in the presence of platinum catalyst, and subjected to a distillation for purification with such a distillation apparatus as shown in the drawing.

First, 2.5 kg of the acrylic silane solution, 0.25 g of phenothiazine, 2.5 g of 2,6-di-t-butyl-4-methylaminomethylphenol, and 0.25 g of dimethyldithiocarbamic acid copper were charged in distillation still (1). After low boiling point components mainly composed of aryl methacrylate were distilled off by reducing the pressure inside the apparatus to 30 kPa and controlling the conditions of distillation column (2) so that the temperature at the top of the column was 60° to 85° C., the pressure was further reduced to 15 kPa and the conditions of the column were controlled again so that the temperature at the top of the column was 69° to 75° C. to obtain the fraction of 3-methacryloxypropyldimethylchlorosilane.

During the distillation, a solution in which N-nitrosophenylhydroxylamine aluminum salt was dissolved in 3-methacryloxypropyldimethylchlorosilane so that the content of the aluminum salt was 2% by weight ratio was supplied from the top portion of distillation column (2) having an inside diameter of about 50 cm and filled up with a "Heli-Pack".

While the distillation for purification was continuously repeated 5 times, the polymerization which increased the viscosity of the acrylic silane solution in distillation still (1) was not observed at the time of the distillation and the formation of the products of proliferous polymerization was not noticed, either. After finishing the distillation, inside of distillation column (2) was inspected to find no products of homogeneous polymerization or proliferous polymerization of acrylic silane.

EXAMPLE 14

Acrylic silane solution containing, as its main component, 3-methacryloxypropyldimethylchlorosilane was produced by a known method from aryl methacrylate and dimethylchlorosilane in the presence of platinum catalyst, and subjected to a distillation for purification with such a distillation apparatus as shown in the drawing.

First, 5 kg of the acrylic silane solution, 0.5 g of phenothiazine, and 0.5 g of dimethyldithiocarbamic acid copper were charged in distillation still (1). After low boiling point components mainly composed of aryl methacrylate were distilled off by reducing the pressure inside the apparatus to 30 kPa and controlling the conditions of distillation column (2) so that the temperature at the top of the column was 60° to 85° C., the pressure was further reduced to 15 kPa and the conditions of the column were controlled again so that the temperature at the top of the column was 69° to 75° C. to obtain the fraction of 3 methacryloxypropyldimethylchlorosilane.

During the distillation, a liquid mixture in which N-nitroso phenylhydroxylamine aluminum salt and 2,6-di-t-butyl-4-methylphenol were mixed with 3-methacryloxypropyldimethylchlorosilane so that the content of the aluminum salt was 2% and that of the phenol was 1% by weight ratio, respectively, was supplied from the top portion of distillation column (2) having an inside diameter of about 50 cm and filled up with a "Heli-Pack".

While the distillation for purification was continuously repeated 5 times, the polymerization which increased the viscosity of the acrylic silane solution in distillation still (1) was not observed at the time of the distillation and the formation of the products of proliferous polymerization was not noticed, either. After finishing the distillation, inside of distillation column (2) was inspected to find no products of homogeneous polymerization or proliferous polymerization of acrylic silane.

Comparative Example 4

Distillation was conducted according to the method in Example 7 except that a solution in which N-nitrosophenylhydroxylamine aluminum salt was dissolved in 3-methacryloxypropyldimethylchlorosilane so that the content of the aluminum salt was 2% by weight ratio was supplied. After low boiling point components mainly composed of aryl methacrylate were distilled off by reducing the pressure inside the distillation apparatus to 15 kPa and controlling the conditions of the column so that the temperature at the top of the column was 30° to 69° C., the products of spontaneous polymerization of acrylic silane were formed inside distillation column (2) to block the distillation column, and thus the distillation procedures became impossible to continue.

Comparative Example 5

Distillation was conducted according to the method in Example 7 except in that a solution in which 2,6-di-t-butyl-4-methylphenol was dissolved in 3-methacryloxypropyldimethylchlorosilane so that the content of the phenol was 2% by weight ratio was added from the top portion of distillation column (2) instead of a solution in which N-nitrosophenylhydroxylamine aluminum salt was dissolved in 3-methacryloxypropyldimethylchlorosilane so that the content of the aluminum salt was 2% by weight ratio in Example 7.

In the course of the time when low boiling point components mainly composed of aryl methacrylate were distilled off by reducing the pressure inside the distillation apparatus to 15 kPa and controlling the conditions of the distillation column so that the temperature at the top of the column was 30° to 69° C., the products of spontaneous polymerization of acrylic silane were formed inside distillation column (2), the products blocked the distillation column, and thus the distillation procedures became impossible to continue.

Comparative Example 6

Distillation was conducted according to the method in Example 7 except in that a solution in which phenothiazine was dissolved in 3-methacryloxypropyldimethylchlorosilane so that the content of phenothiazine was 2% by weight ratio was added from the top portion of distillation column (2) instead of a solution in which N-nitrosophenylhydroxylamine aluminum salt was dissolved in 3-methacryloxypropyldimethylchlorosilane so that the content of the aluminum salt was 2% by weight ratio in Example 7.

In the course of the time when low boiling point components mainly composed of aryl methacrylate were distilled off by reducing the pressure inside the distillation apparatus to 15 kPa and controlling the conditions of the distillation column so that the temperature at the top of the column was 30° to 69° C., the products of spontaneous polymerization of acrylic silane were formed inside distillation column (2), the products blocked the distillation column, and thus the distillation procedures became impossible to continue.

From the Examples and Comparative Examples mentioned above, it can be seen that when a hindered phenol and/or amine is used together with a dialkyldithiocarbamic acid copper and/or N-nitrosophenylhydroxylamine salt, the spontaneous polymerization of acrylic silane, which will be caused when acrylic silane is produced in a commercial scale without using such combination of the compounds, can be repressed.

As will be understood from Referential Example mentioned above, whereas proliferous polymerization is not caused at a beaker test, it is caused when a scale up of the distillation is made to a level of Comparative Example 1. Accordingly, it is dangerous to make the scale up of the distillation based on the results of a beaker scale test of conventional test methods. However, since the distillation process of the present invention is based on the investigation in an actual commercial scale, acrylic silane can commercially be produced without any problems.

Whereas dialkyldithiocarbamic acid copper and N-nitrosophenylhydroxylamine salt are poor in their effect on repressing polymerization in a beaker scale test so that they have not been used as preferable polymerization inhibitor, it has now been found by the present inventors that when dialkyldithiocarbamic acid copper and/or N-nitrosophenylhydroxylamine salt was used together with a hindered phenol and/or amine in a level of commercial scale, the former exhibits an extremely large effect on repressing polymerization.

Further, it has been found that in the case of using a distillation apparatus comprising a distillation still and distillation column, when distillation is conducted while supplying a liquid mixture containing a N-nitrosophenylhydroxylamine salt or containing the amine salt and a hindered phenol and/or amine from an upper portion of distillation column, the spontaneous polymerization of acrylic silane, which is apt to be caused when a acrylic silane solution is distilled for purification in a commercial scale in the absence the amine salt, can be very efficiently repressed, and that the spontaneous polymerization of acrylic silane can be repressed even when the distillation is repeated.

We claim:

1. In a process for distilling a crude acrylic silane solution for separating acrylic silane expressed by formula (I) by distilling the crude acrylic silane solution in the presence of a hindered phenol and/or amine as polymerization inhibitor by using a distillation apparatus provided with a distillation still and a distillation column arranged above the distillation still, the improvement comprising conducting the distillation while adding a liquid mixture containing a N-nitrosophenylhydroxylamine salt as further polymerization inhibitor from an upper portion of the distillation column

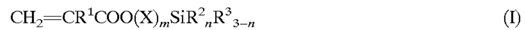

$$CH_2{=}CR^1COO(X)_mSiR^2_nR^3_{3-n} \qquad (I)$$

wherein $R^1$ represents hydrogen atom, an alkyl group having 1 to 8 carbon atoms, or an aryl group having 6 to 10 carbon atoms, X represents $CH_2CH_2O$ or $CH_2$, or combination of these two groups, m is an integer of 1 to 12, $R^2$ represents a hydrolyzable group, $R^3$ represents an alkyl group, alkenyl group, or aryl group having 1 to 12 carbon atoms, and n is an integer of 1 to 3.

2. The process for distilling a crude acrylic silane solution according to claim 1 wherein the liquid mixture further contains a hindered phenol and/or amine.

3. The process for distilling a crude acrylic silane solution according to claim 1 wherein the N-nitrosophenylhydroxylamine salt is a compound expressed by formula (II)

$$(R^4N(NO)O)_pY_q \qquad (II)$$

wherein $R^4$ represents an aryl group having 6 to 10 carbon atoms, p is an integer of 1 to 4, q is an integer of 1 to 4, and Y represents a cation atom or molecule.

4. The process for distilling a crude acrylic silane solution according to claim 1 wherein the hindered phenol is a compound having, in the vicinity of a hydroxyl group of an aromatic ring, at least one substituent causing steric hindrance in the compound.

5. In a process for distilling a crude acrylic silane solution for separating acrylic silane expressed by formula (I) by distilling the crude acrylic silane solution in the presence of a hindered phenol and/or amine as polymerization inhibitor, the improvement comprising adding simultaneously a N-nitrosophenylhydroxylamine salt as further polymerization inhibitor to the solution $$CH_2{=}CR^1COO(X)_mSiR^2_nR^3_{3-n} \qquad (I)$$

wherein $R^1$ represents hydrogen atom, an alkyl group having 1 to 8 carbon atoms, or an aryl group having 6 to 10 carbon atoms, X represents $CH_2CH_2O$ or $CH_2$, or combination of these two groups, m is an integer of 1 to 12, $R^2$ represents a hydrolyzable group, $R^3$ represents an alkyl group, alkenyl group, or aryl group having 1 to 12 carbon atoms, and n is an integer of 1 to 3.

6. The process for distilling a crude acrylic silane solution according to claim 5 wherein the hindered phenol is a compound having, in the vicinity of a hydroxyl group of an aromatic ring, at least one substituent causing steric hindrance in the compound.

7. The process for distilling a crude acrylic silane solution according to claim 5 wherein the nitrosophenylhydroxylamine salt is added in generated vapor at the time of distillation.

8. The process for distilling a crude acrylic silane solution according to claim 5 wherein the N-nitrosophenylhydroxylamine salt is a compound expressed by formula (II)

$$(R^4N(NO)O)_pY_q$$

wherein $R^4$ represents an aryl group having 6 to 10 carbon atoms, p is an integer of 1 to 4, q is an integer of 1 to 4, and Y represents a cation atom or molecule.

9. The process for distilling a crude acrylic silane solution according to claim 5 wherein a dialkyldithiocarbamic acid copper is added simultaneously as an additional further polymerization inhibitor.

10. The process for distilling a crude acrylic silane solution according to claim 9, wherein the dialkyldithiocarbamic acid copper is a compound expressed by formula (III)

$$(R^5{}_2NC(=S)S)_2Cu \quad \text{(III)}$$

wherein $R^5$ represents an alkyl group having 1 to 5 carbon atoms.

11. The process for distilling a crude acrylic silane solution according to claim 9 wherein the distillation is conducted in a distillation still by adding the dialkyldithiocarbamic acid copper and/or N-nitrosophenylhydroxylamine salt in the distillation still prior to the initiation of distillation.

12. The process for distilling a crude acrylic silane solution according to claim 5 wherein the distillation is conducted while adding the N-nitrosophenylhydroxylamine salt in a liquid mixture from an upper portion of a distillation column.

13. The process for distilling a crude acrylic silane solution according to claim 12 wherein the liquid mixture contains the N-nitrosophenylhydroxylamine salt and the hindered phenol and/or amine.

* * * * *